(12) United States Patent
Belau et al.

(10) Patent No.: US 6,921,570 B2
(45) Date of Patent: Jul. 26, 2005

(54) PATTERN UNBONDED NONWOVEN WEB AND PROCESS FOR MAKING SAME

(75) Inventors: Tom R. Belau, Neenah, WI (US); Timothy J. Blenke, Neenah, WI (US); Richard T. Wehrle, New London, WI (US); Rebecca J. Kuepper, Appleton, WI (US); Thomas D. Ehlert, Neenah, WI (US); Alan F. Schleinz, Apppleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 229 days.

(21) Appl. No.: 10/036,851

(22) Filed: Dec. 21, 2001

(65) Prior Publication Data

US 2003/0119404 A1 Jun. 26, 2003

(51) Int. Cl.$^7$ .............................. B32B 3/06; B32B 9/00; D02G 3/00; D04H 5/00; A61F 13/20
(52) U.S. Cl. ...................... 428/103; 428/100; 428/359; 442/361; 442/394; 442/381; 604/385.01
(58) Field of Search ................................ 442/394, 401, 442/381, 361; 604/379, 385.01, 386; 428/103, 104, 195, 99, 100, 101, 102, 170, 156, 163

(56) References Cited

U.S. PATENT DOCUMENTS

| | | |
|---|---|---|
| 3,082,817 A | 3/1963 | Merrill |
| 3,276,944 A | 10/1966 | Levy |
| 3,338,992 A | 8/1967 | Kinney |
| 3,341,394 A | 9/1967 | Kinney |
| 3,423,266 A | 1/1969 | Davies et al. |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,766,922 A * | 10/1973 | Krusko ...................... 604/374 |
| 3,802,817 A | 4/1974 | Matsuki et al. |
| 4,088,726 A | 5/1978 | Cumbers |
| 4,340,563 A | 7/1982 | Appel et al. |

(Continued)

FOREIGN PATENT DOCUMENTS

| | | | |
|---|---|---|---|
| EP | 1 048 236 A2 | 11/2000 | |
| GB | 1 499 178 | 1/1978 | |
| JP | 01271242 | 10/1989 | |
| WO | WO 99/27879 | * 6/1999 | ........... A61F/13/46 |
| WO | WO 01/49230 A1 | 7/2001 | |

OTHER PUBLICATIONS

International Search Report dated Feb. 6, 2003 in PCT/US 02/32486.

*Primary Examiner*—Terrel Morris
*Assistant Examiner*—Lynda Salvatore
(74) *Attorney, Agent, or Firm*—Senniger Powers

(57) ABSTRACT

The present invention provides a pattern-unbonded material that has at least two distinct regions. One region has different bond pattern than another region. The different bond pattern provides different, specific functionality or characteristics to the material. In an embodiment, the one region provides an optimal mechanical fastener, hook engagement. The different characteristics include, but are not limited to, opacity, tensile strength or stiffness. The different characteristics are provided by a bond pattern specific to the particular region. The outer regions, in an embodiment, are stronger and appear more substantial by being more opaque than or color-shifted relative to an inner region. The outer regions, in an embodiment, are not directly backed or supported by the garment to which the material is attached. Accordingly, it is important for the outer regions to provide adequate strength, stiffness, color, and opacity absent the garment backing the outer regions.

29 Claims, 8 Drawing Sheets

U.S. PATENT DOCUMENTS

| | | |
|---|---|---|
| 4,704,116 A | 11/1987 | Enloe |
| 4,761,318 A | 8/1988 | Ott et al. |
| 4,902,366 A | 2/1990 | Bader |
| 5,032,122 A | 7/1991 | Noel et al. |
| 5,133,707 A | 7/1992 | Rogers et al. |
| 5,226,992 A | 7/1993 | Morman |
| 5,326,612 A | 7/1994 | Goulait |
| 5,399,174 A * | 3/1995 | Yeo et al. .................... 604/365 |
| 5,418,045 A | 5/1995 | Pike et al. |
| 5,496,298 A | 3/1996 | Kuepper et al. |
| 5,540,796 A | 7/1996 | Fries |
| 5,595,618 A | 1/1997 | Fries et al. |
| 5,707,468 A | 1/1998 | Arnold et al. |
| 5,858,515 A * | 1/1999 | Stokes et al. ............. 428/195.1 |

* cited by examiner

PATTERN UNBONDED NONWOVEN WEB AND PROCESS FOR MAKING SAME

FIELD OF THE INVENTION

The present invention generally relates to the field of nonwoven fabrics and webs, and processes for manufacturing same. More specifically, the present invention relates to nonwoven fabrics and webs having a pattern unbonded area.

BACKGROUND

Mechanical fastening systems, of the type otherwise referred to as hook and loop fastener systems, have become increasingly widely used in various consumer and industrial applications. A few examples of such applications include disposable personal care absorbent articles, clothing, sporting goods equipment, and a wide variety of other miscellaneous articles. Typically, such hook and loop fastening systems are employed in situations where a refastenable connection between two or more materials or articles is desired. These mechanical fastening systems have in many cases replaced other conventional devices used for making such refastenable connections, such as buttons, buckles, zippers, and the like.

Mechanical fastening systems typically employ two components, a male (hook) component and a female (loop) component. The hook component usually includes a plurality of semi-rigid, hook-shaped elements anchored or connected to a base material. The loop component generally includes a resilient backing material from which a plurality of upstanding loops project. The hook-shaped elements of the hook component are designed to engage the loops of the loop material, thereby forming mechanical bonds between the hook and loop elements of the two components. These mechanical bonds function to prevent separation of the respective components during normal use. Such mechanical fastening systems are designed to avoid separation of the hook and loop components by application of a shear force or stress, which is applied in a plane parallel to or defined by the connected surfaces of the hook and loop components, as well as certain peel forces or stresses. However, application of a peeling force in a direction generally perpendicular or normal to the plane defined by the connected surfaces of the hook and loop components can cause separation of the hook elements from the loop elements, for example, by breaking the loop elements and thereby releasing the engaged hook elements, or by bending the resilient hook elements until the hook elements disengage the loop elements.

Mechanical fastening systems can be advantageously employed in disposable personal care absorbent articles, such as disposable diapers, disposable garments, disposable incontinence products, and the like. Such disposable products generally are single-use items which are discarded after a relatively short period of use, usually a period of hours, and are not intended to be washed and reused. As a result, it is desirable to avoid expensive components in the design of such products. Thus, to the extent that the hook and loop components are employed in such products, the hook and loop components need to be relatively inexpensive in terms of both the materials used and the manufacturing processes for making these components. On the other hand, the hook and loop components must have sufficient structural integrity and resiliency to withstand the forces applied thereto during normal wear of the absorbent article, in order to avoid potentially embarrassing situations for the wearer that can result from premature separation or disengagement of the hook and loop components.

U.S. Pat. No. 4,761,318 to Ott et al. discloses a loop fastening material useful in a mechanical fastening system for disposable articles. The loop fastening material disclosed by this patent includes a fibrous layer having a plurality of loops on a first surface adapted to be releasably engaged by a mating hook fastener portion and a layer of thermoplastic resin adhered to a second surface of the fibrous structure opposite the first surface. The thermoplastic resin anchors the loops in the fibrous structure.

U.S. Pat. No. 5,032,122 to Noel et al. discloses a loop fastening material useful in a mechanical fastening system for a disposable article. The loop fastening material disclosed by this patent includes a backing of orientable material and a multiplicity of fibrous elements extending from the backing. The fibrous elements are formed by continuous filaments positioned on and intermittently secured to the backing when the orientable material of the backing is in its dimensionally unstable state. The fibrous elements are formed by the shirring of the filaments between spaced, fixed regions of securement to the backing when the orientable material is caused to be transformed to its dimensionally stable state such that it is caused to contract or gather along its path of response. Thus, the loop material of this patent requires a backing of orientable material, such as an elastic or elastomeric or heat shrinkable material, that is caused to be transformed from a dimensionally stable state to a dimensionally unstable state and returned it to its dimensionally stable state.

U.S. Pat. No. 5,133,707 to Rogers et al. discloses a composite adhesive fastening tape and tape system for interconnecting printed surfaces, which includes a transparent main film portion with an embossed surface defined logo or symbol or the like and coated on one surface with an adhesive, in the tape system is included a target film portion, which target film portion is optionally decorated by colored numbers, letters, patterns, shapes or figures.

U.S. Pat. No. 5,326,612 to Goulait discloses another a loop fastening material useful in a mechanical fastening system for a disposable article. The loop fastening material disclosed by this patent includes a nonwoven web secured to a backing. The nonwoven web serves to admit and entangle the hooks of a complementary hook component. The nonwoven web has a specified basis weight range of between about 5 to about 42 g/m$^2$, an inter-fiber bond area of less than about 10 percent, and a total plan view bonded area of less than about 35 percent.

U.S. Pat. No. 5,858,515 to Stokes et al., herein incorporated by reference, discloses a pattern-unbonded nonwoven fabric having continuous bonded areas defining a plurality of discrete unbonded areas, which is suitable for use as an improved loop fastening material for hook and loop fastening systems. The fibers or filaments within the discrete unbonded areas are dimensionally stabilized by the continuous bonded areas that encircle or surround each unbonded area. The spaces between fibers or filaments within the unbonded areas remain sufficiently open or large to receive and engage hook elements of a complementary hook material. The hook material is any of a wide variety of commercially available hook components which include a base material from which a plurality of hook elements project. Stokes et al. further describe a process for making such a pattern-unbonded nonwoven fabric including the steps of providing a nonwoven fabric or web, providing oppositely positioned first and second calender rolls and defining a nip therebetween, with at least one of the rolls being heated and having a bonding pattern on its outermost surface comprising a continuous pattern of land areas defining a plurality of discrete recesses, apertures or holes, and passing the nonwoven fabric or web within the nip formed by said rolls.

Notwithstanding the teachings of the aforementioned references, the need nonetheless exists for an improved pattern-unbonded, nonwoven fabric. Moreover, there still exists a need for an improved region of a web or fabric including loop fastening material for a mechanical fastening system, particularly as such are used in disposable personal care absorbent articles.

SUMMARY

In response to the difficulties and problems discussed herein, a new nonwoven web including a pattern unbonded area is presented herein. Specifically, the present invention provides a pattern unbonded area that has a plurality of regions that have different characteristics. In an embodiment, the different characteristics are provided by one region having an unbonded pattern that differs from an unbonded pattern of another region. In an embodiment, the differing characteristic is opacity. In an embodiment, the differing characteristic is tensile strength. In an embodiment, the differing characteristic is color. In an embodiment, the differing characteristic is stiffness. In an embodiment, the pattern unbonded area is part of a mechanical fastening system. In an embodiment, the mechanical fastening system is part of a garment. In an embodiment, the garment is a disposable personal care absorbent article. In an embodiment, the article is a diaper.

In an embodiment, the disposable absorbent article of the present invention includes an article chassis having a side edge and a pattern-unbonded material on the article chassis, the pattern-unbonded material including a region that extends beyond the side edge. The region extending beyond the side edge has different characteristics than a portion of the material that is on the article chassis.

In an embodiment, the disposable absorbent article of the present invention includes a mechanical fastening tab joined to the article, the fastening tab including a male component, and a female component joined to the article and adapted for releasable engagement with the male component. The female component includes a fabric having at least two regions defined by different pattern-unbonded patterns or layouts.

A process for forming a pattern-unbonded nonwoven fabric of the present invention includes bonding a nonwoven web by application of heat and pressure to form on a surface thereof a pattern of continuous bonded areas defining a first plurality of discrete unbonded areas and a second plurality of discrete unbonded areas. The first plurality of discrete unbonded areas provide a characteristic that differs from the second plurality of discrete unbonded areas.

In an embodiment, the present invention includes a mechanical fastening system that includes a male component and a female component adapted to receive the male component. The female component is formed in a receiving area that includes a first region and a second region. The first region includes a first pattern of discrete unbonded area that form a female component adapted for releasable engagement with the male component. The second region includes a second pattern of discrete, unbonded areas that are different than the first pattern.

Other embodiments of the present invention will be appreciated by one of skill in the art upon reading the present disclosure.

BRIEF DESCRIPTION OF THE DRAWINGS

The present invention is illustrated by way of example in the following drawings in which like reference characters indicate similar elements throughout the several views. The following drawings disclose various embodiments of the present invention for purposes of illustration only and are not intended to limit the scope of the invention.

DETAILED DESCRIPTION OF THE INVENTION

Figure 1:
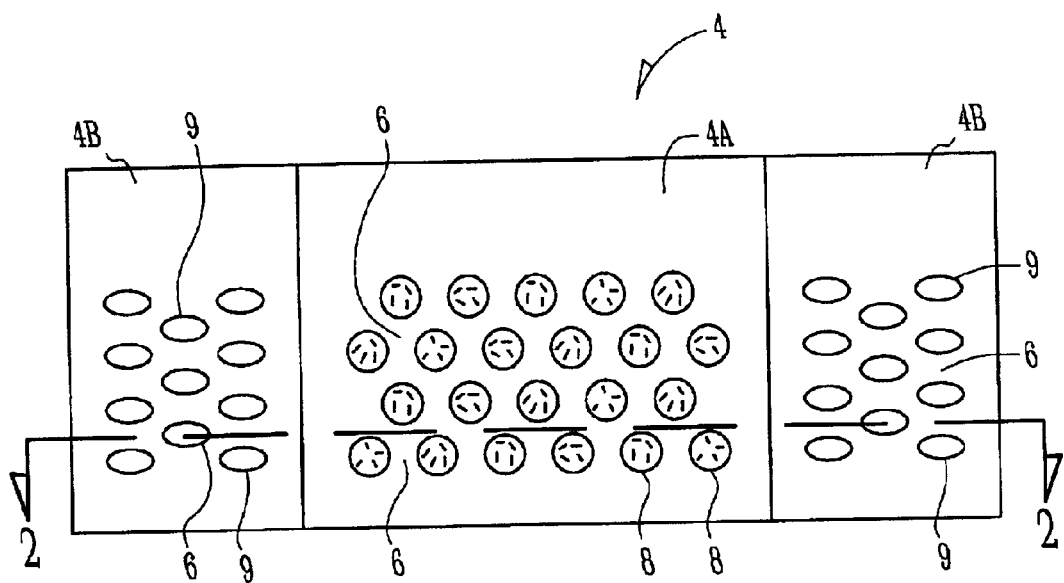
FIG. 1 is a top elevational view of the pattern-unbonded nonwoven fabric of the present invention.

The present invention relates to a nonwoven fabric or web having continuous bonded areas defining a plurality of discrete, unbonded areas in at least two distinct regions. One of the regions is suitable for use as loop fastening material for a mechanical or hook and loop fastening system. The plurality of discrete, unbonded areas are divided into a plurality of sub-areas, regions or zones that have differing characteristics. For purposes of illustration only, the present invention will be described as a loop fastening material both separately and in conjunction with its use with disposable personal care absorbent articles, which include diapers, training pants, incontinence garments, sanitary napkins, bandages and the like. As such, the invention should not be limited to these specific uses, unless recited in the claims, as it is instead intended that the present invention be used in all applications in which such pattern-unbonded nonwoven fabric or web can be suitably employed.

For example, the pattern-unbonded nonwoven fabric or web of the present invention can be utilized as a filtration material, as well as a fluid management or distribution material for personal care absorbent articles, such as bodyside liners or surge materials used in disposable diapers and the like. The continuous bonded areas of the pattern-unbonded nonwoven web are substantially fluid impermeable, while the discrete unbonded areas of the web remain fluid permeable. Thus, the pattern-unbonded web includes discrete or isolated unbonded areas that function as specific fluid flow points or channels. Moreover, the regions of the discrete, isolated unbonded areas have different characteristics. The combination of continuous bonded areas and discrete unbonded areas within the pattern-unbonded web can be utilized to direct and channel fluid flow. Moreover, the pattern unbonded regions can further be utilized to direct and channel fluid flow within the unbonded areas. Moreover, the pattern of continuous bonded areas and discrete unbonded areas can be modified to provide a variety of desired arrangements of flow points or channels for fluid filtration, management or distribution by modifying the pattern-unbonding assembly. Moreover, the pattern unbonded regions can further be utilized to provide a variety of desired arrangements of flow points or channels for fluid filtration, management or distribution by modifying the pattern of unbonded regions. Moreover, the three-dimensional surface topography of the pattern-unbonded fabric of the present invention can provide an aesthetically pleasing appearance for its user. Moreover, the pattern unbonded regions can further be utilized to provide an aesthetically pleasing, unbonded area appearance for the user.

When used as the female or loop component of a hook and loop fastening system, the loop material of the present invention is intended to be utilized with a wide variety of hook materials. Exemplary of hook materials suitable for use with the loop material of the present invention are those obtained from: Velcro Group Company, of Manchester, N.H., H., under the trade designations HTH-851, HTH-853, or HTH-864; or Minnesota Mining & Manufacturing Co., of St. Paul, Minn., under the designation CS 600. Suitable hook materials generally include from about 16 to about 620 hooks per square centimeter, or from about 124 to about 388 hooks per square centimeter, or from about 155 to about 310 hooks per square centimeter. The hooks suitably have a height of from about 0.00254 centimeter (cm) to about 0.19 centimeter, or from about 0.0381 centimeter to about 0.0762 centimeter.

Hook materials typically include a base layer with a plurality of uni- or bi-directional hook elements extending generally perpendicularly therefrom. As used herein, the term "bi-directional" refers to a hook material having individual adjacent hook elements oriented in opposite directions in the machine direction of the hook material. The term "uni-directional," on the other hand, refers to a hook material having individual adjacent hook elements oriented in the same direction in the machine direction of the hook material. Hook elements have an average overall height measured from the top surface of the base material to the highest point on the hook elements. The average height of the hook elements used in conjunction with the present invention is about 0.5 millimeter (mm). This hook material has a hook density of about 265 hooks per square centimeter. The thickness of the base material is about 3.5 mils. This hook material is available from Velcro U.S.A. as HTH-851. Other dimensions and properties of the hook material are within the scope of the present invention.

Although the term "hook material" is used herein to designate the portion of a mechanical fastening system having engaging (hook) elements, it is not intended to limit the form of the engaging elements to only include "hooks" but shall encompass any form or shape of engaging element, whether unidirectional or bi-directional, as is known in the art to be designed or adapted to engage a complementary loop fastening material, such as the pattern-unbonded nonwoven loop material of the present invention.

Figure 2:
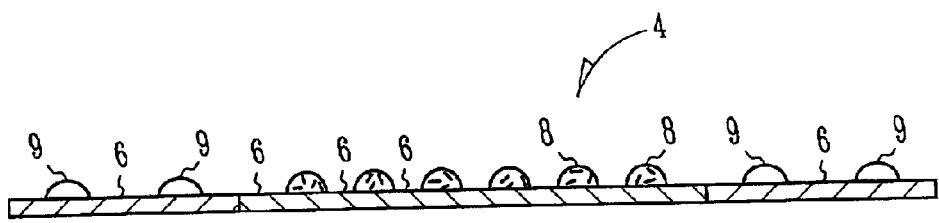
FIG. 2 is a cross-sectional view of the pattern-unbonded nonwoven fabric taken generally along line 2—2 of FIG. 1.

Referring to FIGS. 1 and 2, an embodiment of the pattern-unbonded nonwoven material 4 of the present invention is illustrated. Material 4 includes continuous bonded areas 6 that define a plurality of discrete, dimensionally-stabilized unbonded areas 8, 9. Within the continuous bonded areas 6, the fibers or filaments of the nonwoven web are thoroughly bonded or fused together, and desirably are non-fibrous, whereas within the unbonded areas 8, 9, the fibers or filaments of the nonwoven fabric or web are substantially or completely free of bonding or fusing and retain their fibrous structure.

Pattern-unbonded nonwoven material 4 is divided into a plurality of regions or zones 4A, 4B, which have different bond patterns in a direction. The different bond patterns provide different, specific functionality or characteristics to the regions 4A and 4B. In an embodiment, the center region 4A of the material 4 provides optimal hook engagement. The outer regions 4B of the material 4 provide different characteristics than the center region 4A. In an embodiment, the different characteristic is opacity. In an embodiment, the different characteristic is color. In an embodiment, the different characteristic is tensile strength. In an embodiment, the different characteristic is stiffness. In other embodiments, other characteristics of the material 4 would differ between regions 4A and 4B as would be understood upon reading the present disclosure. The different characteristics are provided by a bond pattern specific to the outer regions 4B. In an embodiment, the outer regions 4B extend outwardly beyond the article, e.g., absorbent garment, to which the material 4 is attached. Thus, outer regions 4B must provide their own strength whereas the center region 4A is directly supported and reinforced by the article. Moreover, outer regions 4B must be aesthetically pleasing and appear to have adequate strength to the consumer. The present invention provides these features in the material 4 by having regions therein with different bond patterns.

In the illustrated embodiment, regions 4B are positioned outwardly of and adjacent to the center region 4A. The first unbonded areas 8 are formed in the first, center region 4A. First, center region 4A is pattern-unbonded nonwoven loop material. By way of definition, the term "pattern-unbonded nonwoven loop material" as used herein is intended to refer to a loop or female component for a hook and loop fastening system that includes, in its simplest form, a nonwoven fabric or web having a first area that includes continuous bonded areas 6 that define a plurality of discrete, dimensionally-stabilized unbonded areas 8. This term is not intended to limit the loop material of the present invention to only nonwoven materials; rather, the loop material of the present invention can be advantageously employed in alternative embodiments in which, for example, the pattern-unbonded nonwoven fabric or web is attached or bonded to a layer of film material. Nor is use of the term "loop" intended to limit the loop material of the present invention to only materials in which discrete, separately formed loops of material are employed to receive and engage the hook elements of a complementary hook material; rather, the loop material of the present invention includes fibrous nonwoven fabrics or webs in which the individual fibers or filaments function to engage the hook elements without such fibers or filaments being formed into discrete loops.

The second unbonded areas 9 are formed in the second region 4B. In an embodiment, second unbonded areas 9 have different characteristics relative to the first unbonded areas 8. For example, the second unbonded areas 9 have at least one different dimension than first unbonded areas 8. The areas 9 may have a cross-machine direction length that is greater than the machine cross direction length of areas 8. The areas 9 may have a cross-machine direction length that is less than the machine cross direction length of areas 8. As used herein, the term "machine direction" or MD means the length of a material or fabric in the direction in which it is produced (from left to right in FIG. 3). The term "cross-machine direction" or CD means the width of a material or fabric, i.e., a direction generally perpendicular to the MD. As shown in FIG. 1, the machine direction is top to bottom. As shown in FIG. 1, the cross-machine direction is left to right. The areas 9 may have a machine direction length that is greater than the machine direction length of areas 8. The areas 9 may have a machine direction length that is less than the machine direction length of areas 8. The areas 9 may have a height, which extends upwardly from the surface of bonded area 6, that is greater than the height of areas 8. In an embodiment, the areas 9 are uniform. In an embodiment, area 8 are uniform.

The regions 4A and 4B, in an embodiment, further differ from each other in the amount of bond area. Bond area is defined as the percent of the area of the bonds relative to the total area In an embodiment, the region 4A has a bond area of about 35% of the total area. In an embodiment, region 4B has a bond area less than 35%. In an embodiment, region 4B has a bond area less than 25%. In an embodiment, region 4B has a bond area less than 15%. In an embodiment, region 4B has a bond area greater than 35%. In an embodiment, region 4B has a bond area greater than 40%. In an embodiment, region 4B has a bond area greater than 50%.

FIG. 1 shows lines separating the regions 4A and 4B. In an embodiment, the bonded area 6 is continuous and not separated between regions 4A and 4B. Accordingly, the lines separating the regions 4A and 4B are merely a visual aid to illustrate different regions on the material 4.

As used herein, the terms "layer" or "web" when used in the singular can have the dual meaning of a single element or a plurality of elements. As used herein, the term "laminate" means a composite material made from two or more layers or webs of material which have been attached or bonded to one another.

Referring again to FIGS. 1 and 2, pattern-unbonded nonwoven loop material region 4A can be generally described as any nonwoven fabric or web that, when formed in accordance with the present invention, is suitable for receiving and engaging the hooks of a complementary hook material. As used herein, the terms "nonwoven fabric" or "nonwoven web" mean a web having a structure of individual fibers or filaments that are interlaid, but not in an identifiable manner as in a knitted fabric. It should be noted, however, that although the present invention will be described in the context of nonwoven fabrics and webs, woven and/or knitted fabrics formed of appropriate materials such that a pattern of continuous bonded areas defining a plurality of discrete unbonded areas could be formed on at least one surface thereof can be dimensionally stabilized employing the process and apparatus described herein.

Commercially available thermoplastic polymeric materials can be advantageously employed in making the fibers or filaments from which pattern-unbonded nonwoven material 4 is formed. As used herein, the term "polymer" shall include, but is not limited to, homopolymers, copolymers, such as, for example, block, graft, random and alternating copolymers, terpolymers, etc., and blends and modifications thereof. Moreover, unless otherwise specifically limited, the term "polymer" shall include all possible geometrical configurations of the material, including, without limitation, isotactic, syndiotactic and random symmetries. As used herein, the terms "thermoplastic polymer" or "thermoplastic polymeric material" refer to a long-chain polymer that softens when exposed to heat and returns to its original state when cooled to ambient temperature. Exemplary thermoplastic materials include, without limitation, poly(vinyl chloride)s, polyesters, polyamides, polyfluorocarbons, polyolefins, polyurethanes, polystyrenes, poly(vinyl alcohol)s, caprolactams, and copolymers of the foregoing. The fibers or filaments used in making pattern-unbonded nonwoven material 4 may have any suitable morphology and may include hollow or solid, straight or crimped, single component, bicomponent or multicomponent, biconstituent or multiconstituent fibers or filaments, and blends or mixes of such fibers and/or filaments, as are well known in the art.

Nonwoven webs that can be employed as the pattern-unbonded nonwoven material of the present invention can be formed by a variety of known forming processes, including spunbonding, airlaying, or bonded carded web formation processes. All such nonwoven webs may be pre-bonded, using known nonwoven web bonding techniques, and subsequently bonded using the pattern-unbonded method and apparatus of the present invention, or alternatively, such nonwoven webs may only be bonded using the pattern-unbonded method and apparatus of this invention.

Spunbond nonwoven webs are made from melt-spun filaments. As used herein, the term "melt-spun filaments" refers to small diameter fibers and/or filaments which are formed by extruding a molten thermoplastic material as filaments from a plurality of fine, usually circular, capillaries of a spinnerette with the diameter of the extruded filaments then being rapidly reduced, for example, by non-eductive or eductive fluid-drawing or other well known spunbonding mechanisms. The production of spunbond nonwoven webs is described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,276,944 to Levy, U.S. Pat. No. 3,502,538 to Peterson, and U.S. Pat. No. 3,542,615 to Dobo et al., all of which are incorporated herein by reference. The melt-spun filaments formed by the spunbond process are generally continuous and have diameters larger than 7 microns, more particularly, between about 10 and 30 microns. Another frequently used expression of fiber or filament diameter is denier, which is defined as grams per 9000 meters of a fiber or filament. The spunbond filaments usually are deposited onto a moving foraminous belt or forming wire where they form a web. Spunbond filaments generally are not tacky when they are deposited onto the collecting surface.

Spunbond fabrics typically are stabilized or consolidated (pre-bonded) in some manner immediately as they are produced in order to give the web sufficient integrity to withstand the rigors of further processing into a finished product. This stabilization (prebonding) step may be accomplished through the use of an adhesive applied to the filaments as a liquid or powder which may be heat activated, or more commonly, by compaction rolls. As used herein, the term "compaction rolls" means a set of rollers above and below the web used to compact the web as a way of treating a just produced, melt-spun filament, particularly spunbond, web, in order to give the web sufficient integrity for further processing, but not the relatively strong bonding of secondary bonding processes, such as through-air bonding, thermal bonding, ultrasonic bonding and the like. Compaction rolls slightly squeeze the web in order to increase its self-adherence and thereby its integrity.

An alternative means for performing the pre-bonding step employs a hot air knife, as described in detail in the commonly assigned U.S. Pat. No. 5,707,468, filed Dec. 22, 1994, which is incorporated herein by reference. Briefly, the term "hot air knife" means a process of pre-bonding a just produced melt-spun filament, particularly spunbond, web, in order to impart the web with sufficient integrity, i.e., increase the stiffness of the web, for further processing, but not the relatively strong secondary bonding processes as noted above. A hot air knife is a device that focuses a stream of heated air at a very high flow rate, generally from about 300 to about 3000 meters per minute (mi/min.), or more particularly from about 900 to about 1500 m/min., directed at the nonwoven web immediately after its formation. The air temperature usually is in the range of the melting point of at least one of the polymers used in the web, generally between about 90 degrees C. and about 290 degrees C. for the thermoplastic polymers commonly used in spunbonding. The control of air temperature, velocity, pressure, volume and other factors helps avoid damage to the web while increasing its integrity. The hot air knife's focused stream of air is arranged and directed by at least one slot of about 3 to about 25 millimeters (mm) in width, particularly about 9.4 mm, serving as the exit for the heated air towards the web, with the slot running in a substantially cross-machine direction over substantially the entire width of the web. In other embodiments, there may be a plurality of slots arranged next to each other or separated by a slight gap. The at least one slot usually, but not necessarily, is continuous, and may be comprised of, for example, closely spaced holes. The hot air knife has a plenum to distribute and contain the heated air prior to its exiting the slot. The plenum pressure of the hot air knife usually is between about 2 to about 22 mmHg, and the hot air knife is positioned between about 6.35 mm and about 254 mm, and more particularly from about 19.05 to about 76.20 mm above the forming surface. In a particular embodiment, the hot air knife plenum's cross-sectional area for cross-directional flow (i.e., the plenum cross-sectional area in the machine direction) is at least twice the total slot exit area. Since the foraminous wire onto which spunbond polymer is formed generally moves at a high rate of speed, the time of exposure of any particular part of the web to the air discharge from the hot air knife typically is less than a tenth of a second and generally about one hundredth of a second, in contrast with the through-air bonding process, which has a much longer dwell time. The hot air knife process has a great range of variability and control over many factors, including air temperature, velocity, pressure, and volume, slot or hole arrangement, density and size, and the distance separating the hot air knife plenum and the web.

Figure 3:
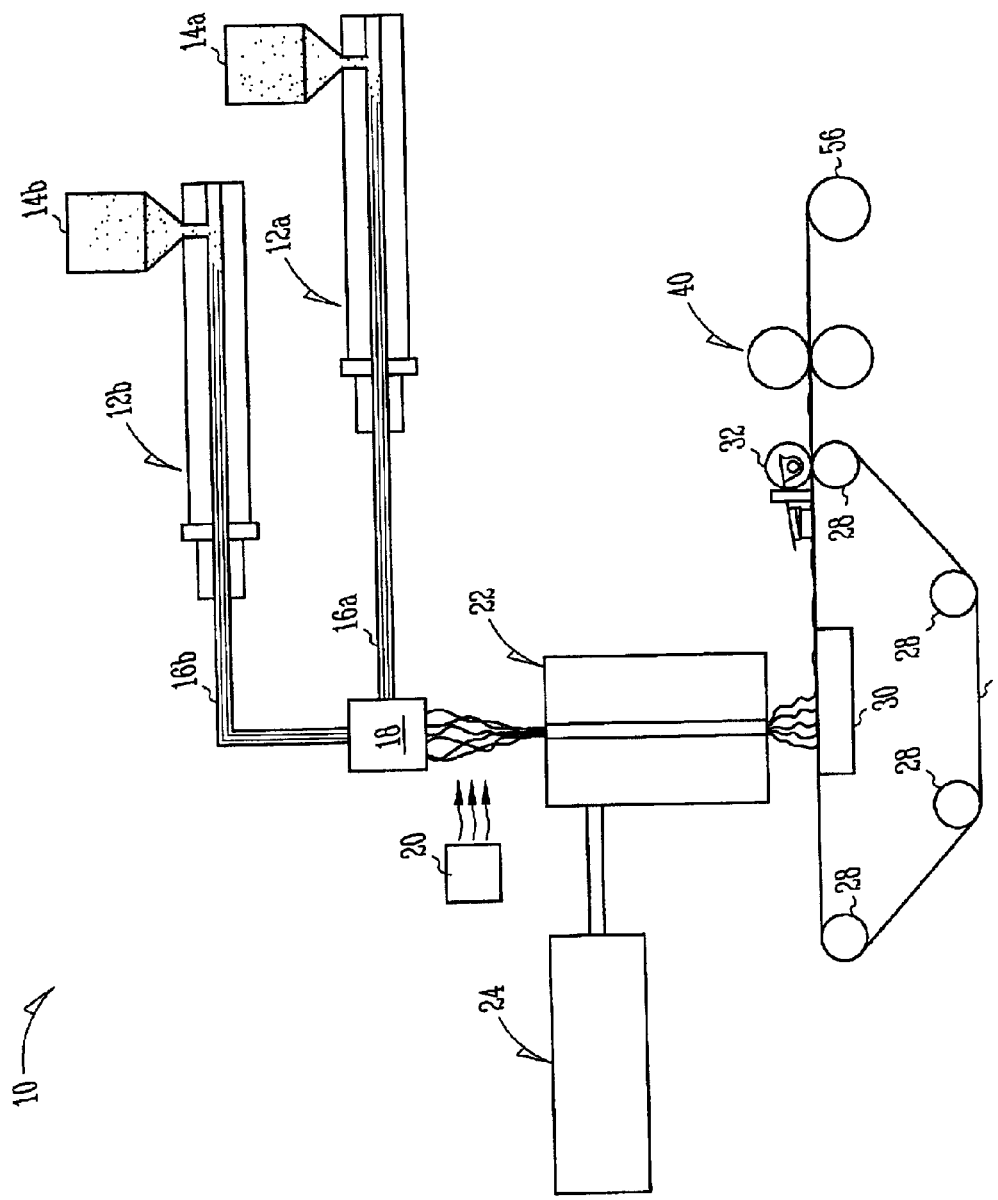
FIG. 3 is a schematic view of a process and apparatus for producing a nonwoven web.

The spunbond process also can be used to form bicomponent spunbond nonwoven webs as, for example, from side-by-side (or sheath/core) linear low density polyethylene/polypropylene spunbond bicomponent filaments. A suitable process for forming such bicomponent spunbond nonwoven webs is described in U.S. Pat. No. 5,418,045 to Pike et al., which is incorporated herein by reference in its entirety. Referring to FIG. 3 hereof, this process line 10 for forming such bicomponent filaments and resultant webs includes using a pair of extruders 12*a* and 12*b* for separately supplying both the polyethylene and the polypropylene from hoppers 14*a* and 14*b*, respectively, through extrusion conduits 16*a* and 16*b*, respectively, to a bicomponent spinnerette 18. Spinnerettes for producing bicomponent filaments are well known in the art and, therefore, are not described herein in detail. Generally, the spinnerette 18 includes a housing containing a spin pack, which includes a plurality of vertically stacked plates having a pattern of openings arranged to create flow paths for directing the high melting temperature and low melting temperature polymers separately to the fiber-forming openings in the spinnerette. The spinnerette 18 has openings arranged in one or more rows and the openings form a downwardly extending curtain of filaments when the polymers are extruded through the spinnerette. A quenching gas source 20 is positioned downstream of the exit from spinnerette 18. As the curtain of filaments exit the spinnerette 18, they are contacted by quenching gas from source 20. Quenching gas impinges one or both (not shown) sides of the filament curtain, which at least partially quenches the filaments and develops a latent helical crimp in the filaments extending from the spinnerette 18. Typically, the quenching air will be directed generally perpendicularly to the length of the filaments at a velocity of from about 30 to about 120 meters per minute and at a temperature of about 7° C. to about 32° C.

A fiber draw unit or aspirator 22 is positioned below, e.g. downstream of, the spinnerette 18 to receive the quenched filaments. Fiber draw units or aspirators for use in melt spinning polymers are known in the art. Exemplary fiber draw units suitable for use in this process include a linear fiber aspirator of the type shown in U.S. Pat. No. 3,802,817 to Matsuki et al., and eductive guns of the type shown in U.S. Pat. No. 3,692,618 to Dorschner et al. and U.S. Pat. No. 3,423,266 to Davies et al., the disclosures of which are incorporated herein by reference in their entirety. The fiber draw unit 22 in general has an elongated passage through which the filaments are drawn by aspirating gas flowing through the passage. The aspirating gas may be any gas, such as air, that does not adversely interact with the polymers of the filaments. A supply unit 24 supplies the aspiratiating gas to the fiber draw unit 22. As the aspirating gas draws the quenched filaments and ambient air through the fiber draw unit 22, the filaments are heated to a temperature that is required to activate the latent crimping therein. The temperature required to activate the latent crimping within the filaments will range from about 43 degrees Celsius to a maximum of less than the melting point of the low melting component polymer which, in this case, is the polyethylene. Generally, a higher air temperature produces a higher number of crimps per unit length of the filament. Alternatively, the curtain of filaments exiting the spinnerette 18 may be drawn at ambient temperature, consequently forming a web of substantially straight or non-crimped spunbond filaments.

The drawn and crimped filaments exit the fiber draw unit 22 and are deposited onto a continuous forming surface 26 in a random manner, generally assisted by a vacuum device 30 placed underneath the forming surface. The purpose of the vacuum is to eliminate the undesirable scattering of the filaments and to guide the filaments onto the forming surface 26 to form a uniform, unbonded, nonwoven web of bicomponent filaments. If desired, the resultant web can be lightly compressed by a compression roller 32 or hot air knife (not shown) before the web is subjected to the pattern-unbonding assembly 40 of the present invention as described herein.

Suitable nonwoven webs for use in making the present invention also may be made from bonded carded webs and airlaid webs, which typically are formed of non-continuous, staple fibers. Care must be exercised when employing such nonwoven webs in making the pattern unbonded nonwoven loop material of the present invention to suitably adapt the size and density of the discrete, unbonded areas to maximize the number of individual fibers within the unbonded areas having at least one portion thereof, and advantageously multiple portions thereof, extending into the bonded areas.

Bonded carded webs are made from staple fibers, which are usually purchased in bales. The bales are placed in a picker, which separates the fibers. Then, the fibers are sent through a combing or carding unit, which further breaks apart and aligns the staple fibers in the machine direction to form a generally machine direction-oriented fibrous nonwoven web. Once the web is formed, it may be pre-bonded as described above.

Airlaying is another well known process by which fibrous nonwoven webs can be formed. In the airlaying process, bundles of small fibers having typical lengths ranging from about 6 to about 19 millimeters (mm) are separated and entrained in an air supply and then deposited onto a forming screen, usually with the assistance of a vacuum supply. The randomly deposited fibers then can be pre-bonded to one another using known bonding techniques.

Figure 4:
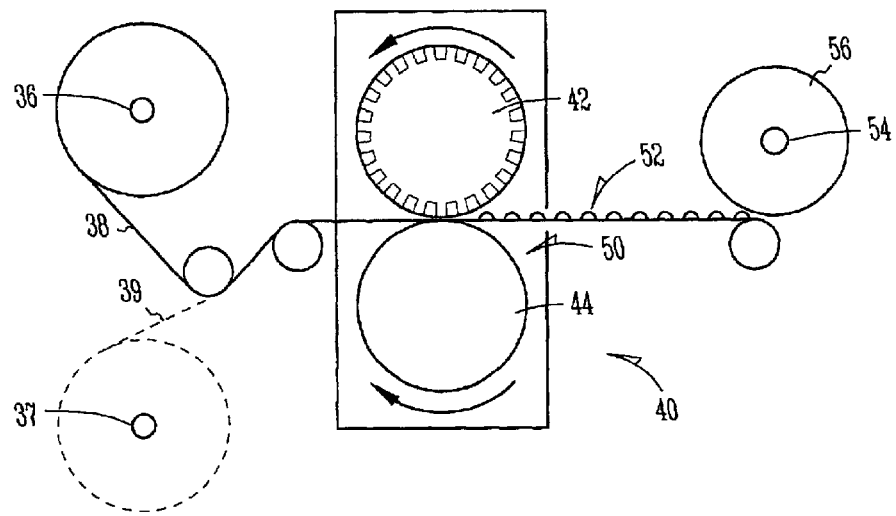
FIG. 4 is a schematic view of a process and apparatus for making the pattern-unbonded nonwoven fabric of the present invention.
Figure 5:
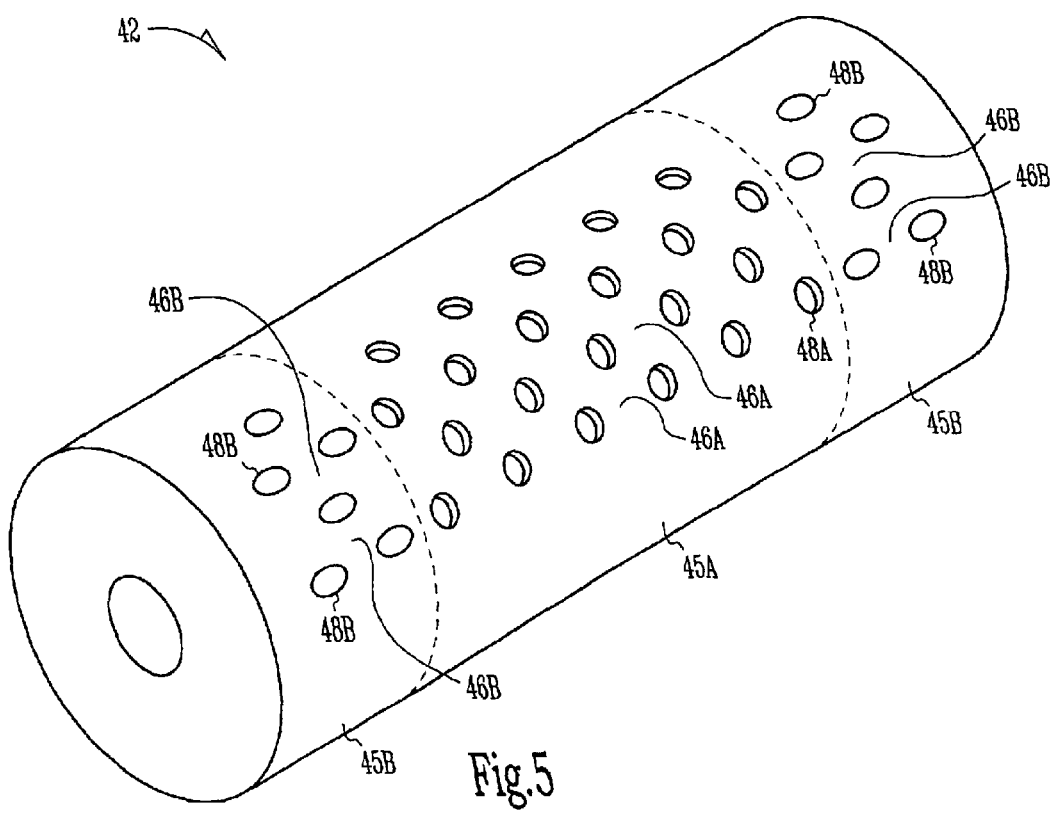
FIG. 5 is a perspective view of a pattern roll that can be used in accordance with the process and apparatus of FIG. 4.

After the nonwoven web is formed, the pre-bonded or unbonded web is passed through a suitable process and apparatus 40 to form the pattern-unbonded nonwoven material 4 of the present invention. Referring now to FIGS. 4 and 5, a process and apparatus for forming the pattern-unbonded nonwoven material 4 of this invention now will be described. In FIG. 4, apparatus for forming the pattern-unbonded nonwoven material 4 of this invention is generally represented at 40. The apparatus 40 includes a first web unwind 36 for a first web 38. Optionally, one or more additional web unwinds 37 (shown in broken line) for additional webs or layers 39 may be employed in forming multi-layer pattern-unbonded laminates. It should be understood that although the apparatus shown in FIG. 4 illustrates a web unwind 36, the pattern-unbonding assembly 40 may be placed in a continuous (in-line) process with the nonwoven forming equipment described herein and as shown in FIG. 3. As used herein, the term "pattern-unbonding assembly" should not be construed as apparatus for disassembling, destroying or removing existing bonds, if any, in web 38; rather, pattern-unbonding assembly refers to an apparatus that continuously bonds or fuses the fibers or filaments forming web 38 in specified areas of the web, and prevents bonding or fusing of the fibers or filaments of web 38 in other specified areas of the web, such areas being referred to herein as bonded areas and unbonded areas, respectively.

First web 38 (or simply "web" if only one unwind is used) is taken off the unwind 36 and passed into a pattern-unbonding assembly 40 that includes a first or pattern roll 42 and a second or an anvil roll 44, both of which are driven, e.g., rotated, by conventional drive means, such as, for example, electric motors (not shown). Pattern roll 42 includes a center surface 45A for forming the center region 4A and a plurality of outer surfaces 45B for forming outer regions 4B. Pattern roll 42 is a right circular cylinder that may be formed of any suitable, durable material, such as, for example, hardened metal or steel, to reduce wear on the rolls during use. Pattern roll 42 has on its outer surface a first pattern of land areas 46A in the center surface 45A. The land areas 46A define a first plurality of discrete recesses or apertures 48A. The land areas 46A are designed to form a nip with the smooth or flat outer surface of oppositely positioned anvil roll 44, which also is a right circular cylinder that can be formed of any suitable, durable material. The land area 46A and apertures 48A form the center region 4A of the pattern-unbonded material 4.

The size, shape, number and configuration of recesses 48A in pattern roll 42 can be varied to meet the particular end-use needs of the pattern-unbonded nonwoven loop material being formed thereby. In order to reduce the incidence of fiber pull-out in the resulting loop material, the size of recesses 48A in center surface 45A of pattern roll 42 should be dimensioned to reduce the likelihood that the entire length of the filaments or fibers forming an unbonded area will lie within a single unbonded area. Stated differently, fiber length should be selected to reduce the likelihood that the entire length of a given fiber or filament will fall within a single unbonded area. On the other hand, the desirability of restricting the size of the recesses 48A in pattern roll 42, and the unbonded areas 8 formed thereby in the center region 4A of pattern-unbonded nonwoven material 4, is counter-balanced by the need for the unbonded areas 8 to have sufficient size to provide the required engagement areas for the hook elements of a complementary hook material. Circular recesses 48A as shown in FIG. 5 hereof having an average diameter ranging from about 0.050 inch (about 0.127 cm) to about 0.250 inch (about 0.635 cm), and more specifically, from about 0.130 inch (0.330 cm) to about 0.160 inch (0.406 cm), and a depth measured from the outermost surface of pattern roll 42 of at least about 0.020 inch (about 0.051 cm), and more particularly at least about 0.060 inch (0.152 cm), are considered suitable in forming the pattern-unbonded nonwoven material of the present invention. While recesses 48A in pattern roll 42 as shown in FIG. 5 are circular, other shapes, such as closed curves, ovals, polygons, squares, diamonds and the like can be advantageously employed.

The number or density of recesses 48A in pattern roll 42 also can be selected to provide the requisite amount of engagement areas for hook elements, without unduly limiting the size of the continuous bonded areas and giving rise to increased incidence of fiber pull-out. Pattern rolls having an recess density in the range of from about 1.0 recess per square centimeter ($cm^2$) to about 25.0 recesses/$cm^2$, and more particularly from about 5.0 to about 7.0 recesses/$cm^2$, may be utilized to advantage in forming the center region 4A of the pattern-unbonded material 4 of the present invention.

Moreover, the spacing between individual recesses 48A can be selected to enhance the hook engagement functionality of the resulting center region 4A of pattern-unbonded material 4, without overly reducing the portion of the pattern-unbonded material occupied by continuous bonded areas, which serve to lessen fiber pull-out. Suitable inter-recess spacings for the embodiment shown can range from about 0.13 inch (about 3.30 mm) to about 0.22 inch (about 5.59 mm), centerline-to-centerline, in the machine and cross-machine directions.

The particular arrangement or configuration of recesses 48A in pattern roll 42 is not considered critical, so long as in combination with the recess size, shape and density, the desired levels of surface integrity and durability and hook element engagement are achieved. For example, as shown in FIG. 5, the individual recesses 48A are arranged in staggered rows (see also FIG. 1). Other different configurations are considered within the scope of the present invention.

The portion of the outermost surface of the pattern roll 42 occupied by continuous land areas 46A likewise can be modified to satisfy the contemplated end-use application of the pattern-unbonded material. The degree of bonding imparted to the center region 4A of the pattern-unbonded nonwoven material 4 by the continuous land areas 46A can be expressed as a percent bond area, which refers to the portion of the total plan area of at least one surface of pattern-unbonded nonwoven material of region 4A, (see FIG. 1) that is occupied by bonded areas 6. Stated generally, the lower limit on the percent bond area suitable for forming the pattern-unbonded nonwoven region 4A of the present invention is the point at which fiber pull-out excessively reduces the surface integrity and durability of the pattern-unbonded material. The required percent bond area will be affected by a number of factors, including the type(s) of polymeric materials used in forming the fibers or filaments of the nonwoven web, whether the nonwoven web is a single- or multi-layer fibrous structure, whether the nonwoven web is unbonded or pre-bonded prior to passing into the pattern-unbonding assembly, and the like. Pattern-unbonded nonwoven materials having percent bond areas ranging from about 25% to about 50%, and more particularly from about 36% to about 50%, have been found suitable.

The pattern roll 42 includes at least two outer surfaces 45B with at least one located longitudinally from each end of the center surface 45A. The outer surfaces 45B of pattern roll 42 includes a second pattern of land areas 46B. The land areas 46B define a second plurality of discrete recesses or apertures 48B. The land areas 46B are designed to form nip 50 with the smooth or flat outer surface of oppositely positioned anvil roll 44. The land area 46B and apertures 48B form the outer regions 4B of the pattern-unbonded material 4.

The size, shape, number and configuration of recesses 48B in pattern roll 42 can be varied to meet the particular end-use needs of the pattern-unbonded nonwoven area 4B being formed thereby. The size of recesses 48B in outer surface 45B of pattern roll 42 are dimensioned to reduce the likelihood that the entire length of the filaments or fibers forming an unbonded area will lie within a single unbonded area 9. Stated differently, fiber length should be selected to reduce the likelihood that the entire length of a given fiber or filament will fall within a single unbonded area 9. Generally oval recesses 48B as shown in FIG. 5 hereof have an average major axis that is less than a value in the range from about 0.050 inch (about 0.127 cm) to about 0.250 inch (about 0.635 cm). In an embodiment, the major axis is less than a value in the range from about 0.130 inch (0.330 cm) to about 0.160 inch (0.406 cm). Oval recesses 48B have an average minor axis that is less than a value in the range from about 0.050 inch (about 0.127 cm) to about 0.250 inch (about 0.635 cm). In an embodiment, the minor axis is less than a value in the range from about 0.130 inch (0.330 cm) to about 0.160 inch (0.406 cm). In an embodiment, the diameter, width, major axis, or minor axis of recesses 48B are less than the diameter of recesses 48A. Oval recesses 48B have a depth measured from the outermost surface of pattern roll 42 of at least about 0.020 inch (about 0.051 cm), and more particularly at least about 0.060 inch (0.152 cm), are considered suitable in forming the pattern-unbonded nonwoven material of the present invention. In an embodiment, the depth of recesses 48B are less than the depth of recesses 48A. While recesses 48B in pattern roll 42 as shown in FIG. 5 are oval, other shapes, such as closed curves, circles, polygons, squares, diamonds and the like can be advantageously employed.

The number or density of recesses 48B in pattern roll 42 also can be selected to provide the requisite characteristics for the outer material areas 4B. Pattern roll outer surfaces 45B may include a recess density in the range of from about 1.0 recess per square centimeter ($cm^2$) to about 25.0 recesses/$cm^2$, and more particularly from about 5.0 to about 7.0 recesses/$cm^2$, may be utilized to advantage in forming the outer region 4B of the pattern-unbonded material 4 of the present invention. In an embodiment, the recess density of outer surfaces 45B is less than the recess density of the center surface 45A. Moreover, the spacing between individual recesses 48B can be selected to enhance and/or provide the requisite characteristic of the outer areas 4B of the material 4. Suitable inter-recess spacings for an embodiment can range from about 0.13 inch (about 3.30 mm) to about 0.22 inch (about 5.59 mm), centerline-to-centerline, in either the machine direction and/or cross-machine direction.

In an embodiment, the inter-recess spacing in the outer surfaces 45B is greater than the inter-recess spacing in the center surface 45A.

The particular arrangement or configuration of recesses 48B in pattern roll 42 is not considered critical, so long as in combination with the recess size, shape and density, the desired levels of surface integrity, durability and characteristic are achieved. For example, as shown in FIG. 5, the individual recesses 48B are arranged in staggered rows (see also FIG. 1). Other different configurations are considered within the scope of the present invention.

The portion of the outermost surface of the pattern roll 42 occupied by continuous land areas 46B likewise can be modified to satisfy the contemplated end-use application of the pattern-unbonded material 4 and, in particular, the end-use application of the pattern-unbonded outer regions 4B. The degree of bonding imparted to the outer region 4B of the pattern-unbonded nonwoven material 4 by the continuous land areas 46B can be expressed as a percent bond area, which refers to the portion of the total plan area of at least one surface of pattern-unbonded nonwoven loop material 4, e.g., region 4B, (see FIG. 1) that is occupied by bonded areas 46B. Stated generally, the lower limit on the percent bond area suitable for forming the pattern-unbonded nonwoven region 4B of the present invention is the point at which fiber pull-out excessively reduces the surface integrity and durability of the pattern-unbonded material 4. The required percent bond area will be affected by a number of factors, including the type(s) of polymeric materials used in forming the fibers or filaments of the nonwoven web, whether the nonwoven web is a single- or multi-layer fibrous structure, whether the nonwoven web is unbonded or pre-bonded prior to passing into the pattern-unbonding assembly, and the like. Pattern-unbonded nonwoven materials having percent bond areas ranging from about 25% to about 50%, and more particularly from about 36% to about 50%, have been found suitable. In an embodiment, the percent bond area of the region 4B is less than the percent bond area of the center region 4A. For example, the percent bond area of the region 4B is less than 50% with the percent bond area of the center region 4A is 50% or greater. The percent bond area of region 4B is less than 36% with when the percent bond area of the center region 4A is 36% or greater. The percent bond area of region 4B is less than 25% with when the percent bond area of the center region 4A is 25% or greater.

It is preferred in the present invention that the pattern-unbonded areas 9 in the outer regions 4B be different than the pattern-unbonded areas 8 in the center, loop fastener region 4A. In an embodiment, the differences between areas 9 and areas 8 include their physical dimensions. The differences between areas 9 and areas 8 result in the respective regions 4B and 4A having different characteristics that are created by the action of pattern roller 42 and anvil roller 44. In an embodiment, the center region 4A is more opaque than the outer region 4B. In an embodiment, the outer region 4B is more opaque than the center region 4A. It will be recognized that the opaqueness may also refer to a color shift that makes the region appear more opaque to the human eye. In an embodiment, the center region 4A is stiffer than the outer region 4B. In an embodiment, the outer region 4B is stiffer than the center region 4A. In an embodiment, the center region 4A has greater tensile strength than the outer region 4B. In an embodiment, the outer region 4B has greater tensile strength than the inner region 4A In general, the outer region 4B has a different bond area pattern than the center region 4A to provide the different characteristics. The characteristics of the outer region 4B are further controlled by changing the percent bond area relative to the percent bond area of the center region 4A. Moreover, any of these characteristics can be combined according to the present invention. For example, the outer regions 4B are stiffer, more opaque, and stronger than the center region 4A.

While the presently described and illustrated embodiment shows a single center region 4A that is flanked on both sides in the cross-machine direction by a single outer region 4B, it is within the scope of the present invention to provide any number of different regions 4A, 4B. For example, two or more outer regions 4B could be provided outwardly in the cross-machine direction from the center, loop region 4A. One of the two or more outer regions 4B, in an embodiment, has at least one different characteristic relative to another of the two or more outer regions 4B.

The illustrated embodiment further shows that the recesses 48A, 48B are at least generally aligned in the lengthwise direction of the cylindrical roller 42. Moreover, recesses 48A, 48B do not extend completely around the circumference of the roller 42 in an embodiment of the present invention. Accordingly, recesses 48A, 48B periodically contact the web 38 to form the discrete pattern-unbonded area 8, 9. In an embodiment, the circumference of the roller 42 is formed equal to the length of one product formed by web 38. For example, if web 38 forms the outer layer of a diaper, then the discrete pattern-unbonded area 8, 9 are formed in web 38 once per revolution of roller 42 for each outer layer. The web 38 is then cut into individual outer layers.

In an embodiment, the pattern roller 42 includes recesses 48A, 48B that are positioned around the circumference of the roller. Thus, pattern unbonded area 8, 9 are formed essentially along the entire length of web 38 as shown at 52 in FIG. 4. The web 38 is then cut in the cross-machine direction to create individual material sections 4. Each individual material section 4 is then bonded to a garment, such as an absorbent garment. The bonding techniques include those discussed herein and others known to one of skill in the art.

The temperature of the outer surface of pattern roll 42 can be varied by heating or cooling relative to anvil roll 44. Heating and/or cooling can affect the features of the web(s) being processed and the degree of bonding of single or multiple webs being passed through the nip 50 formed between the counterrotating pattern roll 42 and anvil roll 44. In the embodiment shown in FIG. 4, for example, both pattern roll 42 and anvil roll 44 are heated, desirably to the same bonding temperature. The specific ranges of temperatures to be employed in forming the pattern-unbonded nonwoven material 4 hereof is dependent upon a number of factors, including the types of polymeric materials employed in forming the pattern-unbonded material, the inlet or line speed(s) of the nonwoven web(s) passing through the nip 50 formed between pattern roll 42 and anvil roll 44, and the nip pressure between pattern roll 42 and anvil roll 44.

Anvil roll 44 as shown in FIG. 4 has an outer surface that is much smoother than pattern roll 42, and preferably is smooth or flat. It is possible, however, for anvil roll 44 to have a slight pattern on its outer surface and still be considered smooth or flat for purposes of the present invention. For example, if anvil roll 44 is made from or has a softer surface, such as resin impregnated cotton or rubber, it will develop surface irregularities, yet it will still be considered smooth or flat for purposes of the present invention. Such surfaces are collectively referred to herein as "flat." Anvil roll 44 provides the base for pattern roll 42 and the web or webs of material to contact. Typically, anvil roll 44 will be made from steel, or materials such as hardened rubber, resin-treated cotton or polyurethane.

Alternatively, anvil roll 44 may be replaced with a pattern roll (not shown) having a pattern of continuous land areas defining a plurality of discrete, apertures or recesses therein, as in the above-described pattern roll 42. In such case, the pattern-unbonding assembly would include a pair of counter-rotating pattern rolls which would impart a pattern of continuous bonded areas defining a plurality of discrete unbonded areas on both the upper and lower surfaces of the pattern-unbonded nonwoven material (i.e., web 38). Rotation of the oppositely positioned pattern rolls can be synchronized, such that the resulting unbonded areas on the surfaces of the pattern-unbonded material are vertically aligned or juxtaposed.

Referring again to FIG. 4, pattern roll 42 and anvil roll 44 are rotated in opposite directions to one another so as to draw the nonwoven web (or webs) through the nip area 50 defined therebetween. Pattern roll 42 has a first rotational speed measured at its outer surface and anvil roll 44 has a second rotational speed measured at its outer surface. In the embodiment shown, the first and second rotational speeds are substantially identical. However, the rotational speeds of the pattern and anvil rolls can be modified to create a speed differential between the counter-rotating rolls.

The locations of the oppositely positioned pattern roll 42 and anvil roll 44 may be varied to create the nip area 50 between the rolls. The nip pressure within nip area 50 can be varied depending upon the properties of the web itself or webs themselves and the degree of bonding desired. Other factors that will allow variances in the nip pressure will include the temperatures of the pattern roll 42 and anvil roll 44, the size and spacing of recesses 48A, 48B in pattern roll 42, as well as the types of polymeric materials used in forming the pattern-unbonded nonwoven material. With respect to the degree of bonding to be imparted to the pattern-unbonded nonwoven material 4 within the continuous bonded areas, the pattern-unbonded material desirably is thoroughly bonded or melt-fused in the bonded areas, such that the polymeric material is rendered non-fibrous. This high degree of bonding is important in stabilizing the portions of the fibers or filaments within the unbonded areas extending into the continuous bonded areas and reducing fiber pull-out when hook elements are disengaged from the discrete unbonded areas.

Figure 6A:
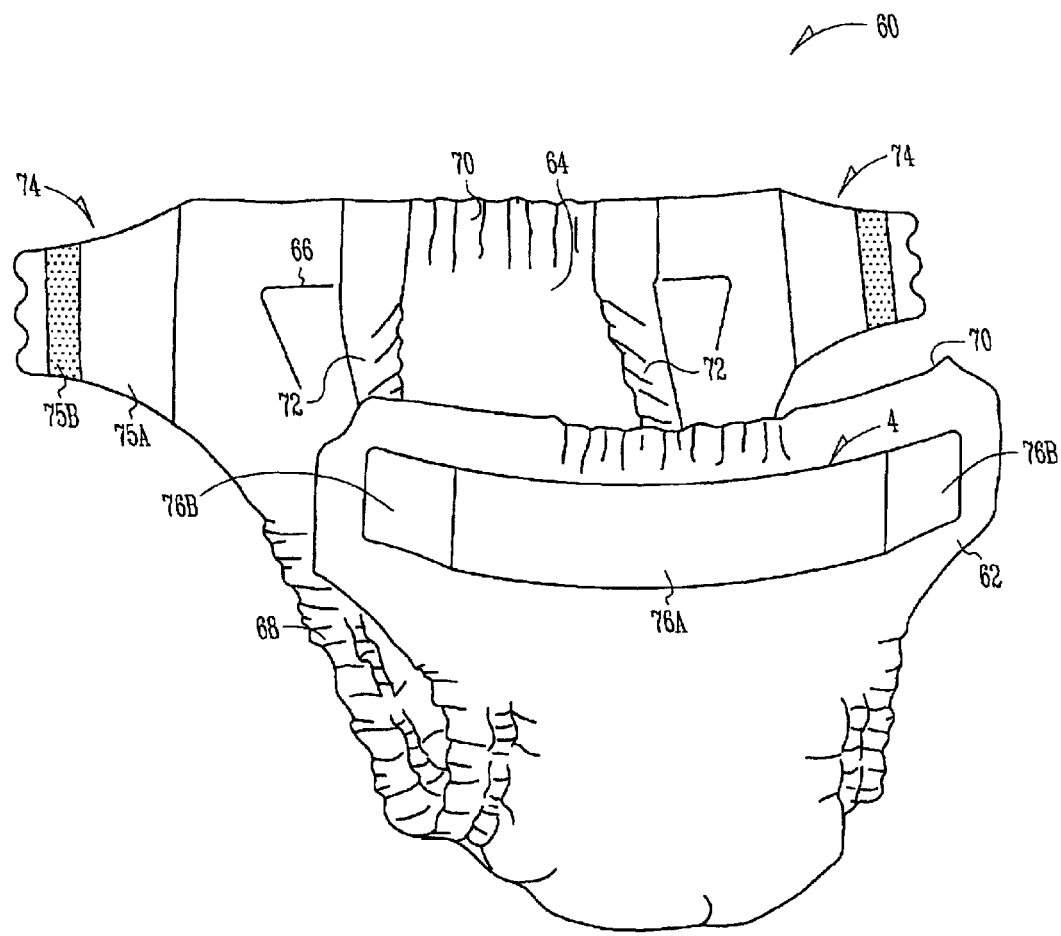
FIG. 6A is a perspective view of a disposable diaper with the pattern-unbonded nonwoven area of the present invention.
Figure 6B:
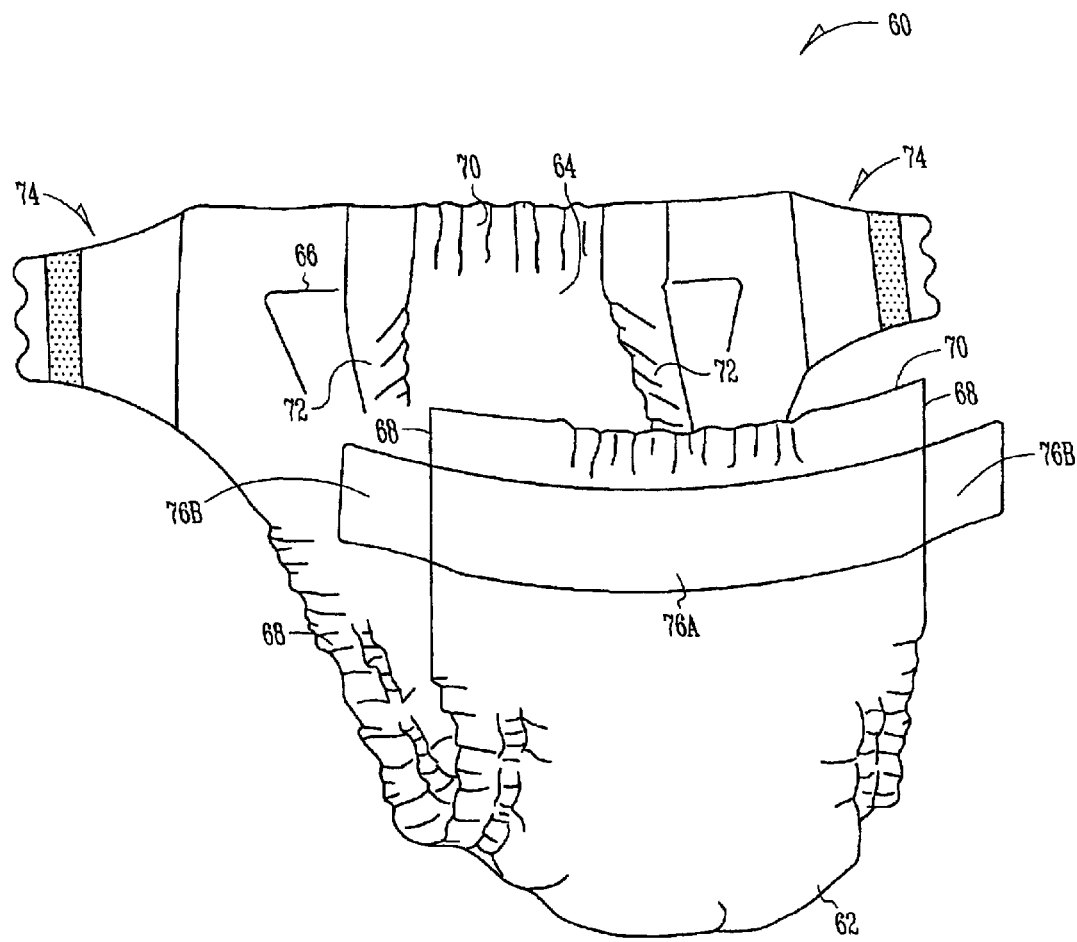
FIG. 6B is a perspective view of a disposable diaper with another embodiment of the pattern-unbonded nonwoven area of the present invention.

Once the pattern-unbonded nonwoven material 4 of the present invention is formed, it can be attached to the outer cover or backsheet of a personal care absorbent article, such as disposable diaper 60 shown in FIGS. 6A and 6B. More specifically, pattern-unbonded material 4 is attached to the outer surface such that the at least one surface of the pattern-unbonded loop material having a pattern of continuous bonded areas defining a plurality of discrete, unbonded areas is exposed. The pattern-unbonded material can be secured to outer cover 62 of diaper 60 by known attachment means, including adhesives, thermal bonding, ultrasonic bonding, or a combination of such means. A wide variety of adhesives can be employed, including, without limitation, solvent-based, water-based, hot-melt and pressure sensitive adhesives. Powdered adhesives can also be applied to the pattern-unbonded loop material and then heated to activate the powder adhesive and perfect bonding.

Diaper 60, as is typical for most personal care absorbent articles, includes a liquid permeable body side liner 64 and a liquid impermeable outer cover 62. Various woven or nonwoven fabrics can be used for body side liner 64. For example, the body side liner may be composed of a meltblown or spunbond nonwoven web of polyolefin fibers, or a bonded carded web of natural and/or synthetic fibers. Outer cover 62 is typically formed of a thin thermoplastic film, such as polyethylene film. The polymer film outer cover may be embossed and/or matte finished to provide a more aesthetically pleasing appearance. Other alternative constructions for outer cover 62 include woven or nonwoven fibrous webs that have been constructed or treated to impart the desired level of liquid impermeability, or laminates formed of a woven or nonwoven fabric and thermoplastic film. Outer cover 62 may optionally be composed of a vapor or gas permeable, "breathable" material, that is permeable to vapors or gas yet substantially impermeable to liquid. Breathability can be imparted in polymer films by, for example, using fillers in the film polymer formulation, extruding the filler/polymer formulation into a film and then stretching the film sufficiently to create voids around the filler particles, thereby making the film breathable. Generally, the more filler used and the higher the degree of stretching, the greater the degree of breathability.

Disposed between liner 64 and outer cover 62 is an absorbent core 66 formed, for example, of a blend of hydrophilic cellulosic woodpulp fluff fibers and highly absorbent gelling particles (e.g., superabsorbent). Absorbent core 66 is generally compressible, conformable, non-irritating to the wearers skin, and capable of absorbing and retaining liquid body exudates. For purposes of this invention, absorbent core 66 can comprise a single, integral piece of material, or a plurality of individual separate pieces of material. The size and absorbent capacity of absorbent core 66 should be compatible with the size of the intended user and the liquid loading imparted by the intended use of the diaper 60.

Elastic members may optionally be disposed adjacent each longitudinal edge 68 of diaper 60. Such elastic members are arranged to draw and hold the lateral, side margins 68 of diaper 60 against the legs of the wearer. Additionally, elastic members also may be disposed adjacent either or both of the end edges 70 of diaper 60 to provide an elasticized waistband.

Diaper 60 may further include optional containment flaps 72 made from or attached to body side liner 64. Suitable constructions and arrangements for such containment flaps are described, for example, in U.S. Pat. No. 4,704,116, to K. Enloe, the disclosure of which is incorporated herein by reference in its entirety.

To secure the diaper 60 about the wearer, the diaper will have some type of fastener or fastening means attached thereto. As shown in FIGS. 6A and 6B, the fastening means is a hook and loop fastening system including a pair of side panels 74 with one attached to each side of the diaper 60. Each side panel 74 includes a stretch sub-panel 75A connected to the diaper chassis, for example, attached to the inner and/or outer surface of outer cover 62 in the one (front or back) of the waistband regions of diaper 60. In some embodiments of the invention the side panels 74 are integrally formed from a layer of material that provides the outer cover or inner cover. In other embodiments, the side panels are formed separately and then attached to the diaper chassis. A hook element panel 75B is outboard of the stretch sub-panel 75A. The hook element panel 75B includes a plurality of the male hook elements, as generally described herein, for attaching the diaper to a wearer. Examples of side panels 74 are described in U.S. Pat. Nos. 5,226,992; 5,496,298; 5,540,796; and 5,595,618, each of which are hereby incorporated by reference.

Diaper 60 further includes one or more loop elements or region 76A made from the pattern-unbonded material 4 of the present invention. In an embodiment, center, loop region 4A is attached to the outer surface of outer cover 62 in the front waistband region of diaper 60.

Diaper 60 includes pattern-unbonded material 4 fixed to the outer cover 62. As shown in FIG. 6A, pattern-unbonded material 4 includes a center region 76A and outer regions 76B spaced outwardly of the center region 76A in the machine cross direction. The center, loop region 76A is backed by the diaper body, which includes at least the outer cover 62 and inner cover 64. The center region 76A includes the loop material to which the hook elements 74 releasably affix. Outer regions 76B extend into a flaps of the diaper 60 and are backed by at least the outer cover 62. Outer regions 76B provide characteristics other than an affixing region for the hook elements. One of the characteristics provided by the outer regions 76B is greater opacity than the center region 76A. This is desired due to the outer regions 76B extending outwardly relative to the diaper chassis. Accordingly, the outer regions 76B, in some embodiments, are not backed by the full depth of the diaper 60, e.g. the inner layer 64 and the absorbent core 66. Consequently, it is desired that the outer regions 76B are more opaque than the center region 76A. Thus, the outer regions 76B due not appear structurally weaker than the center region 76A. Moreover, the outer regions 76B are not used as loop area for the fastening system. Thus, the outer regions 76B can be formed with greater strength than the center region 76A. Strength can be measured as either tensile strength.

FIG. 6B shows a further embodiment of diaper 60, wherein the outer regions 76B of material 4 extend outwardly beyond the diaper chassis. Specifically, the outer regions 76B extend at least partially over the edge 68 of diaper 60. Accordingly, outer regions 76B are not backed or reinforced by the diaper chassis and, more specifically, the outer cover 62, absorbent core 66, or inner cover 64. Stated another way, the outer regions 76B are cantilevered from the diaper chassis and/or the center region 76A. Thus, the outer regions 76B of material 4 must be stronger than the center region 76A, which is directly connected to, supported and reinforced by the diaper chassis. The strength of the regions, in an embodiment, are measured as tensile strength in the cross direction of the web of material 4. It is also important to provide a different appearance for the outer regions 76B relative to center region 76A as outer regions 76B are not backed by the diaper chassis. This is important to provide an aesthetically pleasing appearance. Moreover, the outer regions 76B should in addition to having adequate strength provide the appearance that they have adequate strength to the consumer. Thus, the outer regions 76B, in some embodiments, are made more opaque than the center region 76A. In an embodiment, the outer regions 76B have a different color than the center region 76A.

Figure 7:
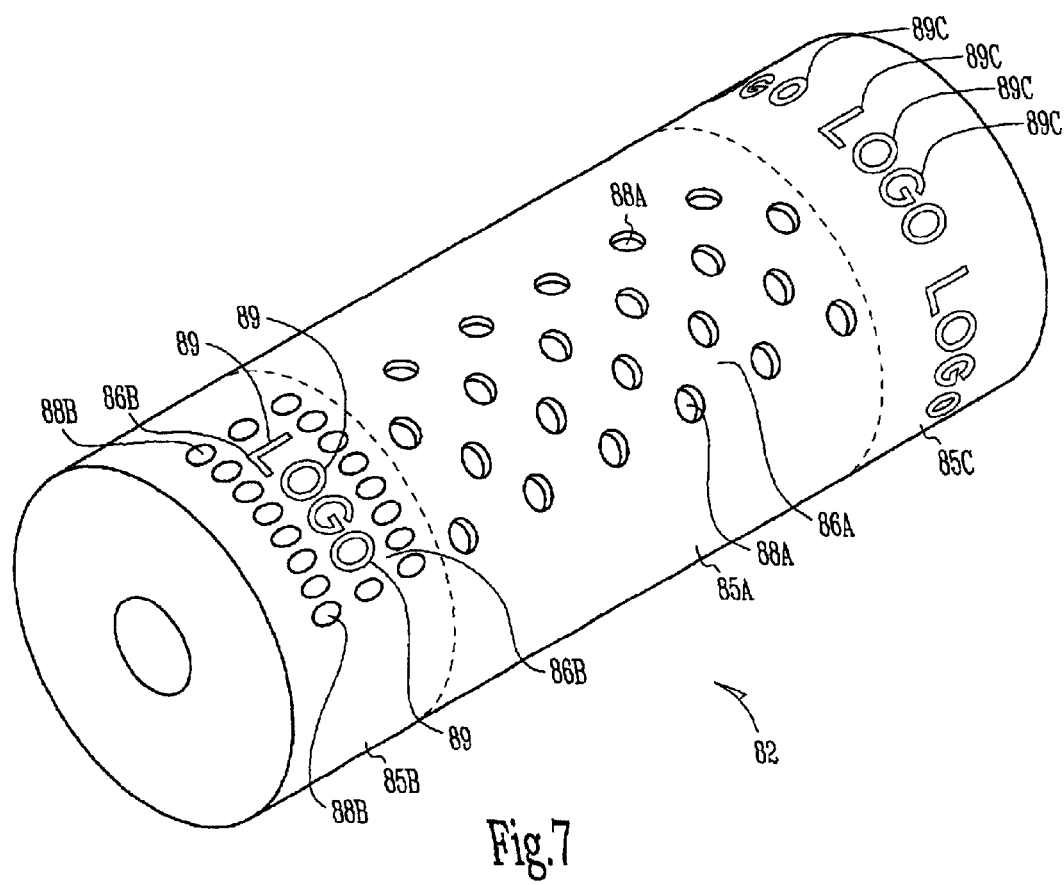
FIG. 7 is a perspective view of an embodiment of a pattern roll that can be used in accordance with the process and apparatus of FIG. 4.

FIG. 7 shows another embodiment of a pattern roller 82, which is used in the pattern-unbonding assembly 40 as described herein. Pattern roller 82 includes a plurality of zones or regions 85A, 85B, 85C. The center region 85A includes the recesses 88A formed within the continuous land pattern 86A. In an embodiment, recesses 88A and land pattern 86A are substantially similar to the center region 45A of roller 42. The first outer region 85B includes recesses 88B formed within a land pattern 86B. In an embodiment, recesses 88B are substantially similar to recesses 48B in the outer region 45B of roller 42. First outer region 85B further includes recesses 89 that are shaped to form specific indicia in web 38. As illustrated the recesses 89 form alphabetic characters, here "LOGO". Such alphabetic character recesses 89 imprint a desired logo on the web 38 and, hence, in an embodiment, diaper 60. In an embodiment, the alphabetic character recesses 89 imprint the desired LOGO in the pattern-unbonded material 4, which is then attached to a garment. The desired logo formed by recesses 89 in land pattern 86B includes, but is not limited to, brand name or size. In other embodiments, the desired logo includes other shapes, forms, or characters that would be aesthetically pleasing to the consumer. Consumer in this instance includes the wearer of the garment having the pattern-unbonded material 4. Examples of the shapes, forms, or characters includes, but is not limited to, geometric shapes, bears, bunnies, farm animals, other child-pleasing characters. Moreover, the recesses 88B are not formed completely around the circumference of roller 82. In operation, recesses 88B create periodic discrete pattern-unbonded areas, e.g., area 91 of FIG. 8. In an embodiment, the recesses 88B are positioned around the entire circumference of the roller 82 and thus pattern-unbond material 4 to continuously bond the web 38 in the machine direction to form discrete pattern-unbonded areas in the web. The web 38 is then cut in the cross-machine direction into individual strips of material 4 that are bonded to an article, such as an absorbent garment, diaper, etc.

The second outer region 85C includes recesses 89C that are shaped to form specific indicia in web 38. As illustrated the recesses 89C form alphabetic characters, here "LOGO". Such alphabetic character recesses 89C imprint a desired logo on the web 38 and, hence, in an embodiment, diaper 60. The recesses 89C extend around the entire circumference of the pattern roller 82. Accordingly, the recesses 89C create discrete unbonded areas that run the entire machine direction, i.e., longitudinal direction of web 38 or machine direction of a diaper 90. Recesses 89C create pattern-unbonded areas such as area 92 in FIG. 8. In an embodiment, the recesses 89C are not formed to extend completely around the roller 82. Accordingly, the discrete pattern-unbonded area formed by recesses 89C are periodically formed in the web.

Figure 8:
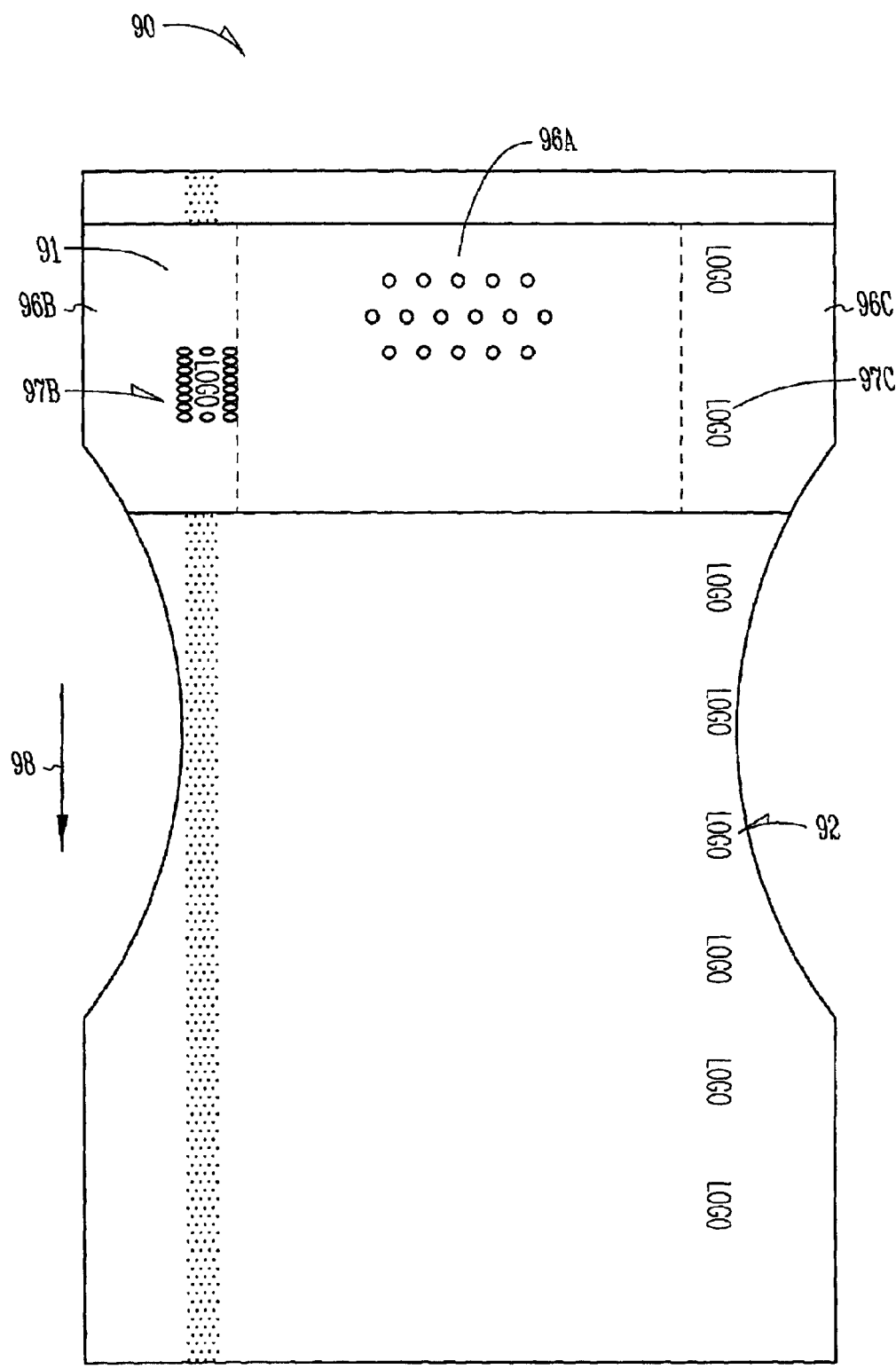
FIG. 8 is a plan view of an outer surface of a disposable diaper with the pattern-unbonded nonwoven area of the present invention.

FIG. 8 shows a plan view of an outer cover of a diaper 90 that is formed using the pattern roller of FIG. 7. The diaper 90 includes a center pattern-unbonded region 96A that includes a plurality of discrete pattern-unbonded areas. These discrete pattern-unbonded areas act as loops in a hook and loop fastening system. The diaper 90 includes outer regions 96B and 96C, which are respectively formed by outer areas of roller 82. Region 96B includes pattern-unbonded areas 97B that represent the pattern of recesses 88B. Pattern unbonded areas 97B are formed only in the region 96B. Region 96C includes pattern-unbonded areas 97C that represent the pattern of recesses 88C. Pattern unbonded areas 97C are formed in both the region 96C and throughout the length of the diaper 90 in the machine direction 98.

EXAMPLE

Figure 9:
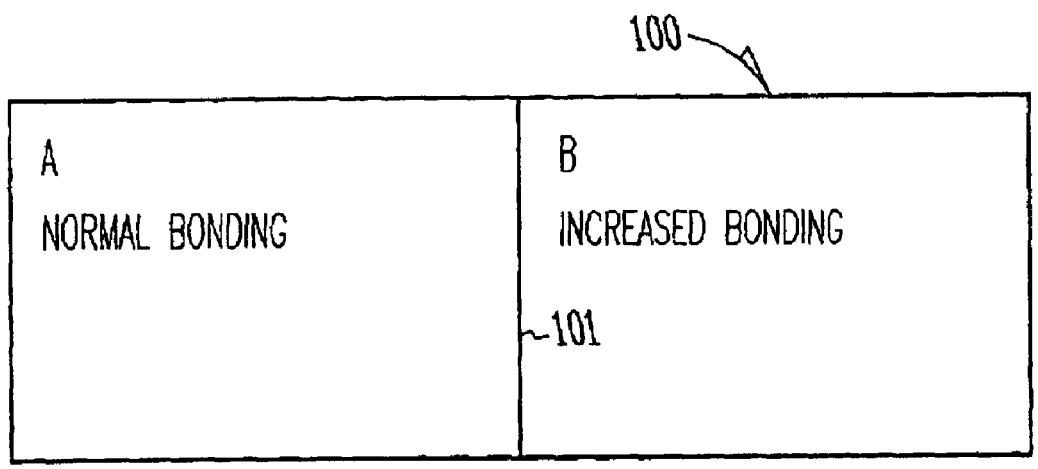
FIG. 9 is a schematic view of a material prepared according to the teachings of the present invention.

An example of a web prepared having two different regions, each region having a different number of discrete pattern-unbonded area was subject to testing for cross-machine direction tensile strength and for color. A first region, designated herein as "A", has a normal bonding pattern that is conventionally used as a center pattern-unbonding loop material. A second region, designated herein as "B", has a bonding pattern that has a decreased number of discrete pattern-unbonded areas and an increased bonded area. The web structure 100 for the testing is schematically shown in FIG. 9. The tested web structure 100 was a two ounces per square yard pattern-unbonded web. The web was a two-layer web having a top layer to bottom layer ratio of 60 to 40 percent. The top layer was nominal 49% polypropylene/48.75% polyethylene copolymer/1.25% optical brightener concentrate/1.0% $TiO_2$ concentrate. The bottom layer was 97.5% polypropylene/1.25% optical brightener concentrate/1.0% $TiO_2$ concentrate. Testing was performed to determine the color and CD tensile strength on each side of the two ounces per square yard pattern-unbonded web samples.

A color test was performed on the samples using the technique described in WIPO publication no. WO 01/49230, which corresponds to PCT application No. PCT/US00/34695. The color of the sample B relative to sample A generally shifted from green to red, i.e., sample B had a more positive "b" value. Therefore, a visual or aesthetic difference was observed. The shift in color will appear to the human eye that the pattern-unbonded sample B is more opaque. The results are shown in Table 1.

Next a cross-machine direction ("CD") tensile test was performed as follows. The sample was cut to three inches wide. The samples were then cut on the dividing line 101 between the A and B sides. The samples of separated A and B sides remained paired together. Next the samples were cut so they were 4.5 inches long. Each sample was tested for CD tensile strength using the test as generally outlined below, modified for 2"×4.5" samples instead of the normal 3"×6". The testing procedure for the CD tensile strength was generally as follows: This test measures the load (strength) in pounds. In the strip tensile test, two clamps, each having two jaws with each jaw having a facing in contact with the sample, hold the material in the same plane, usually vertically, separated by 2 inches and move apart at a specified rate of extension. Values for strip tensile strength and strip elongation are obtained using a sample size of 2 inches by 4.5 inches, with a jaw facing size of 1 inch high by 3 inches wide, and a constant rate of extension of 300 mm/min. The Sintech 2 tester, available from the Sintech Corporation, 1001 Sheldon Dr., Cary, N.C. 27513, the Instron Model TM, available from the Instron Corporation, 2500 Washington St., Canton, Mass. 02021, or a Thwing-Albert Model INTELLECT II available from the Thwing-Albert Instrument Co., 10960 Dutton Rd., Phila., Pa. 19154 may be used for this test. Results are reported as the tensile strength per sample in the cross-machine direction (CD). The results are set forth in Table 2. The CD tensile for code B (more highly bonded pattern-unbonded sample side) is higher than code A (normal bonded pattern-unbonded sample side): Code A avg CD tensile=13.43 lbs; Code B avg CD tensile=22.76 lbs. Accordingly, the more highly bonded, code B sample side was stronger then the normal, loop providing sample side A. In an embodiment of the present invention a Code A pattern is used for the center region 4A, 76A or 96A. In an embodiment of the present invention a Code B pattern is used for the outer region 4B, 76B or 96B.

TABLE 1

| Test Results Color | | | |
|---|---|---|---|
| Code | b | Code | b |
| A | −0.3 | B | −0.21 |
| A | −0.26 | B | −0.02 |
| A | −0.24 | B | 0.04 |

TABLE 1-continued

Test Results
Color

| Code | b | Code | b |
|---|---|---|---|
| A | −0.11 | B | −0.26 |
| A | −0.02 | B | −0.11 |
| A | −0.14 | B | 0.04 |
| A | −0.01 | B | −0.09 |
| A | −0.17 | B | −0.19 |
| A | −0.3 | B | −0.21 |
| A | −0.2 | B | 0.04 |
| A | −0.18 | B | −0.19 |
| A | −0.15 | B | 0.05 |
| A | −0.43 | B | −0.19 |
| A | −0.23 | B | 0.06 |
| A | −0.2 | B | −0.02 |
| A | −0.16 | B | 0.1 |
| A | −0.17 | B | −0.14 |
| A | −0.13 | B | −0.07 |
| A | −0.24 | B | −0.17 |
| A | −0.23 | B | −0.2 |
| avg | −0.1935 | | −0.087 |
| std dev | 0.095161 | | 0.114253 |

TABLE 2

CD Tensile Strength

| Code | lbs | Code | lbs |
|---|---|---|---|
| A | 11.57 | B | 23.42 |
| A | 11.75 | B | 23.38 |
| A | 14.59 | B | 23.95 |
| A | 15.3 | B | 18.34 |
| A | 14.42 | B | 23.4 |
| A | 12.95 | B | 24.05 |
| avg | 13.43 | avg | 22.75667 |
| std dev | 1.570669 | std dev | 2.183856 |

CONCLUSION

The present invention provides a pattern-unbonded material that has at least two distinct regions. One of the regions provides a mechanical fastener receiving area. The other region has different bond pattern than the mechanical fastener region. The different bond pattern provides different, specific functionality or characteristics to the receiving area. In an embodiment, the center area of the receiving area provides optimal mechanical fastener, hook engagement. The outer regions of the material provide different characteristics than the center area. The different characteristics include, but are not limited to, color, opacity, tensile strength or stiffness. The different characteristics are provided by a bond pattern specific to the outer portions. The outer regions, in an embodiment, provide are stronger and appear more substantial by being more opaque. The outer regions, in an embodiment, are not directly backed or supported by the garment to which the material is attached. Accordingly, it is important for the outer regions to provide adequate strength, stiffness, and opacity absent the garment backing the outer regions.

What is claimed is:

1. A pattern-unbonded nonwoven fabric, comprising:
a nonwoven web having a fibrous structure of individual fibers or filaments;
the nonwoven web having on a surface thereof a pattern of continuous bonded areas defining a first plurality of discrete unbonded areas and a second plurality of discrete unbonded areas;
the first plurality of discrete unbonded areas having a first opacity level; and
the second plurality of discrete unbonded areas having a second opacity level, the second opacity level being higher than the first opacity level.

2. A pattern-unbonded non-woven web, comprising:
a first region including a first pattern of continuous bonded areas defining a first plurality of discrete unbonded areas;
at least one second region including a second pattern of continuous bonded areas defining a second plurality of discrete unbonded areas, the second pattern being different from the first pattern, the first region having a first opacity level and the second region having a second opacity level, the second opacity level being higher than the first opacity level.

3. The fabric of claim 1, wherein the first plurality of discrete unbonded areas have a first tensile strength, and the second plurality of discrete unbonded areas have a second tensile strength, the second tensile strength being greater than the first tensile strength.

4. The fabric of claim 1, wherein the first plurality of discrete unbonded areas have a first stiffness, and the second plurality of discrete unbonded areas have a second stiffness different from the first stiffness.

5. The web of claim 2, wherein the first pattern of continuous bonded areas have a first tensile strength, and the second pattern of continuous bonded areas have a second tensile strength, the second tensile strength being greater than the first tensile strength.

6. The web of claim 2, wherein the first pattern of continuous bonded areas have a first stiffness, and the second pattern of continuous bonded areas have a second stiffness different from the first stiffness.

7. The fabric of claim 1, wherein at least a portion of the individual fibers or filaments within the first plurality of discrete unbonded areas extend into and are bonded within the continuous bonded area.

8. The fabric of claim 7, wherein at least a portion of the individual fibers or filaments within the second plurality of discrete unbonded extend into and are bonded within the continuous bonded areas.

9. The fabric of claim 8, wherein the continuous bonded areas comprise from about 25 percent to about 50 percent of the nonwoven web.

10. The fabric of claim 1, wherein the nonwoven web includes melt-spun filaments.

11. The fabric of claim 10, wherein said nonwoven web includes melt-spun filaments, including multicomponent filaments.

12. The fabric of claim 9, wherein the nonwoven web includes staple fibers.

13. The fabric of claim 1, further comprising a film layer attached to a surface of the nonwoven web opposite the surface having the pattern of continuous bonded areas defining the first plurality of discrete unbonded areas, and the second plurality of discrete unbonded areas.

14. The fabric of claim 1, further comprising a second nonwoven web having a fibrous structure of individual fibers or filaments, the second nonwoven web being laminated to the first nonwoven web.

15. The fabric of claim 3, wherein the second tensile strength is about twenty-two pounds.

16. The fabric of claim 3, wherein the first tensile strength is about thirteen pounds.

17. The fabric of claim 3, wherein the second tensile strength is about nine pounds greater than the first tensile strength.

18. The fabric of claim 4, wherein the first stiffness is greater than the second stiffness such that the nonwoven web in a region including the second plurality of discrete unbonded areas more easily bends.

19. The fabric of claim 4, wherein the second stiffness is greater than the first stiffness.

20. The web of claim 2, wherein the first region is adapted for fastening engagement with a hook-type fastener.

21. The web of claim 2, wherein the at least one second region is adjacent the first region in a machine cross direction of the web.

22. The web of claim 2, wherein the at least one second region includes a transition region adjacent the first region, and wherein the transition region includes a third pattern of continuous bonded areas defining a third plurality of discrete unbonded areas, the third pattern being a gradient from the first pattern to the second pattern.

23. The web of claim 5, wherein the second tensile strength is about twenty-two pounds.

24. The web of claim 5, wherein the first tensile strength is about thirteen pounds.

25. The web of claim 5, wherein the second tensile strength is about nine pounds greater than the first tensile strength.

26. The web of claim 6, wherein the first stiffness is greater then the second stiffness such that the nonwoven web in a region including the second plurality of discrete unbonded areas more easily bends.

27. The web of claim 6, wherein the second stiffness is greater than the first stiffness.

28. A disposable absorbent article comprising the pattern-unbonded nonwoven fabric of claim 1.

29. A disposable absorbent article, comprising:

a bodyside liner;

an outer cover, an absorbent structure disposed between the liner and the outer cover;

a mechanical fastening tab joined to the article, the fastening tab including a male fastening component; and a female component joined to the outer cover and adapted for releasable engagement with the male component, the female component comprising the pattern-unbonded nonwoven fabric of claim 1.

* * * * *

UNITED STATES PATENT AND TRADEMARK OFFICE
CERTIFICATE OF CORRECTION

PATENT NO. : 6,921,570 B2  
APPLICATION NO. : 10/036851  
DATED : December 15, 2006  
INVENTOR(S) : Tom R. Belau et al.

It is certified that error appears in the above-identified patent and that said Letters Patent is hereby corrected as shown below:

On the title page: Item [75] should read, --Tom R. Belau as sole inventor--.

Signed and Sealed this

Sixteenth Day of January, 2007

JON W. DUDAS  
*Director of the United States Patent and Trademark Office*

UNITED STATES PATENT AND TRADEMARK OFFICE
CERTIFICATE OF CORRECTION

| | |
|---|---|
| PATENT NO. | : 6,921,570 B2 |
| APPLICATION NO. | : 10/036851 |
| DATED | : July 26, 2005 |
| INVENTOR(S) | : Tom R. Belau et al. |

It is certified that error appears in the above-identified patent and that said Letters Patent is hereby corrected as shown below:

On the title page: Item [75] should read, --Tom R. Belau as sole inventor--.

This certificate supersedes Certificate of Correction issued January 16, 2007.

Signed and Sealed this

Sixth Day of February, 2007

JON W. DUDAS
*Director of the United States Patent and Trademark Office*